(12) United States Patent
Li et al.

(10) Patent No.: US 9,067,956 B2
(45) Date of Patent: Jun. 30, 2015

(54) ZEOLITE POROUS METAL BIS(IMIDAZOLE) COORDINATION POLYMERS AND PREPARATION METHOD THEREOF

(76) Inventors: Dan Li, Shantou (CN); Xiaoping Zhou, Shantou (CN); Jie Liu, Shantou (CN)

( * ) Notice: Subject to any disclaimer, the term of this patent is extended or adjusted under 35 U.S.C. 154(b) by 0 days.

(21) Appl. No.: 14/118,158

(22) PCT Filed: Sep. 14, 2011

(86) PCT No.: PCT/CN2011/079640
§ 371 (c)(1),
(2), (4) Date: Nov. 15, 2013

(87) PCT Pub. No.: WO2012/155417
PCT Pub. Date: Nov. 22, 2012

(65) Prior Publication Data
US 2014/0088312 A1    Mar. 27, 2014

(30) Foreign Application Priority Data

May 16, 2011    (CN) .......................... 2011 1 0125667

(51) Int. Cl.

| | | |
|---|---|---|
| *B01J 20/22* | (2006.01) | |
| *C07F 1/08* | (2006.01) | |
| *C07F 3/00* | (2006.01) | |
| *C07F 15/04* | (2006.01) | |
| *C07F 13/00* | (2006.01) | |
| *C07F 1/00* | (2006.01) | |
| *C07F 3/06* | (2006.01) | |

(52) U.S. Cl.
CPC ............... *C07F 15/045* (2013.01); *B01J 20/22* (2013.01); *C07F 13/005* (2013.01); *C07F 1/005* (2013.01); *C07F 3/00* (2013.01); *C07F 1/08* (2013.01); *C07F 3/06* (2013.01)

(58) Field of Classification Search
CPC ............ B01J 20/22; C07F 1/005; C07F 1/08; C07F 3/00; C07F 3/06; C07F 13/005; C07F 1/0455
See application file for complete search history.

(56) References Cited

PUBLICATIONS

Sunatsuki et al. "Structures and Spin States of Bis(tridentate)-Type Mononuclear and Triple Helicate Dinuclear Iron(II) Complexes of Imidazole-4-carbaldehyde azine" Inorgnaic Chemistry, 2009, vol. 48, pp. 8784-8795.*
Sunatsuki et al., "Structures and Spin States of Bis(tridentate)-Type Mononuclear and Triple Helicate Dinuclear Iron(II) Complexes of Imidazole-4-carbaldehyde azine," Inorg. Chem., vol. 48, pp. 8784-8795 (2009).
Sunatsuki et al., "Mononuclear Bis(tridentate)-Type and Dinuclear Triple Helicate Iron(II) Complexes Containing 2-Ethyl-5-methylimidazole-4-carbaldehyde Azine," Bull. Chem. Soc. Jpn., vol. 82, No. 12, pp. 1497-1505 (2009).
Fujita et al., "Spin States of Mono- and Dinuclear Iron(II) Complexes with Bis(imidazolylimine) Ligands," Chem. Letts. of Chem. Soc. of Jpn., vol. 36, No. 10, pp. 1284-1285 (2007).

* cited by examiner

*Primary Examiner* — Joseph Kosack

(57) ABSTRACT

The present invention discloses zeolite metal bis(imidazole) coordination polymers and preparation method thereof. The new class of zeolite coordination polymers of the present invention is a chemical compound with the following general chemical formula $\{[M(BIm)] \times xDMF \times yC_2H_6O \times zH_2O\}_\infty$, in which when M=Zn, x=0.9, y=0, z=0; when M=Cu, x=1.2, y=0, z=0; when M=Mn, x=2.0, y=0, z=0; when M=Ni, x=0.4, y=1.2, z=1.0, BIm is 1,2-bis((5H-imidazol-4-yl)methylene) hydrazine, DMF is N,N-dimethyl formamide, $H_2O$ is water. A solvothermal method or slow diffusion is used on the compounds to obtain crystals of high purity. The coordination polymers of the present invention have good thermal stability, and have strong adsorption performance for $CO_2$ under conditions of 0° C. and normal pressure as adsorbent materials.

7 Claims, 13 Drawing Sheets

BIm        DMF

ZEOLITE POROUS METAL BIS(IMIDAZOLE) COORDINATION POLYMERS AND PREPARATION METHOD THEREOF

BACKGROUND OF THE INVENTION (a) Field of the Invention

The present invention relates to the field of transition metal coordination materials involving porous metal-organic coordination polymer materials, and in particular to a new class of zeolite porous metal bis(imidazoe) coordination polymers and preparation thereof, in which the microporous coordination polymers belong to a class of three-dimensional zeolite coordination polymers having micropores with a high adsorption capacity for $CO_2$.

(b) Description of the Prior Art

Because of the catalytic, adsorption, and separation properties of zeolites, they have wide application in the industrial fields of petrochemicals, and fine chemicals, as well as in the pharmaceutical-chemical industry. In recent years, zeolite porous metal imidazole coordination polymers have aroused great interest, not only because they have a zeolite network structure, but also, more importantly, because of their extreme stability and potential applications in catalysis, separation, and gas storage (for example: a) Tian, Y. Q.; Cai, C. X.; Ji, Y.; You, X. Z.; Peng, S. M.; Lee, G. H., *Angew. Chem. Int. Ed.* 2002, 41, 1384; b) Huang, X. C.; Lin, Y. Y.; Zhang, J. P.; Chen, X. M., *Angew. Chem. Int. Ed.* 2006, 45, 1557; c) Park, K. S.; Ni, Z.; Côté, A. P.; Choi, J. Y.; Huang, R.; Uribe-Romo, F. J.; Chae, H. K.; O'Keeffe, M.; Yaghi, O. M., *Proc. Natl. Acad. Sci. U.S.A.* 2006, 103, 10186; d) Tran, U. P. N.; Le, K. K. A.; Phan, N. T. S., *ACS Catalysis* 2011, 1, 120-127; e) Jiang, H.-L.; Akita, T.; Ishida, T.; Haruta, M.; Xu, Q., *J. Am. Chem. Soc.* 2011, 133, 1304-1306; f) Venna, S. R.; Carreon, M. A., *J. Am. Chem. Soc.* 2010, 132, 76-78; g) Zhang, J.; Wu, T.; Zhou, C.; Chen, S.; Feng, P.; Bu, X., *Angew. Chem. Int. Ed.* 2009, 48, 2542; h) Wu, T.; Zhang, J.; Zhou, C.; Wang, L.; Bu, X.; Feng, P., *J. Am. Chem. Soc.* 2009, 131, 6111-6113; i) Li, K.; Olson, D. H.; Seidel, J.; Emge, T. J.; Gong, H.; Zeng, H.; Li, J., *J. Am. Chem. Soc.* 2009, 131, 10368-10369; j) Banerjee, R.; Furukawa, H.; Britt, D.; Knobler, C.; O'Keeffe, M.; Yaghi, O. M., *J. Am. Chem. Soc.* 2009, 131, 3875.). Although some porous metal imidazole frameworks with zeolite structures have been synthesized by chemists (only nine types), however, this is still a relatively small number compared to the huge family of 194 types of zeolites (see Baerlocher, C.; Meier, W. M.; Olson, D. H., Atlas of Zeolite Framework Types. 2007; or website: http://www.iza-structure.org/). Hence, synthesis of new types of coordination polymers with zeolite structures is still a major problem. Within the family of 194 types of zeolites, there are only six types of zeolites with a chiral spiral channel structure, among which the BSV zeolite is one of the more exceptional types. The BSV molecular has a three-dimensional channel structure of two types including left-handed spiral channels and right-handed spiral channels. The two channel structures are mirror images of each other. Coordination polymers having three-dimensional spiral channels similar to the BSV zeolite with two types of channel structures including right-handed spiral channels and left-handed spiral channels hitherto have not been reported. Due to the ability to be used in the development of chiral catalysis, and chiral separation materials, the synthesis of and search for such compounds, especially through the rational design of coordination polymers having three-dimensional spiral channels, will have a great impact on the development of high-performance materials, and will inject enormous life into the entire zeolite materials science.

SUMMARY OF THE INVENTION

The object of the present invention is to provide four types of coordination polymers with the same zeolite structure having three-dimensional spiral channels, including zinc-1,2-bis((5H-imidazol-4-yl)methylene)hydrazine, copper-1,2-bis((5H-imidazol-4-yl)methylene)hydrazine, manganese-1,2-bis((5H-imidazol-4-yl)methylene)hydrazine, and nickel-1,2-bis((5H-imidazol-4-yl)methylene)hydrazine.

Another object of the present invention is to provide a preparation method for the zeolite porous coordination polymers.

A further object of the present invention is to provide zeolite porous coordination polymers with application as materials for $CO_2$ adsorption and storage.

The technical proposal of the present invention is as follows: a zeolite porous coordination polymer having the formula: $\{[M(BIm)] \times xDMF \times yC_2H_6O \times zH_2O\}_\infty$, wherein M is selected from Zn, Cu, Mn or Ni, and when M=Zn, x=0.9, y=0, z=0; when M=Cu, x=1.2, y=0, z=0; when M=Mn, x=2.0, y=0, z=0; and when M=Ni, x=0.4, y=1.2, z=1.0. The polymer structure is shown in FIG. 15.

BIm is 1,2-bis((5H-imidazol-4-yl)methylene)hydrazine, DMF is N,N-dimethyl formamide. Structures of BIm and DMF are shown in FIG. 16.

The main infrared absorption peaks of the coordination polymers described in the present invention are as follows: zinc-1,2-bis((5H-imidazol-4-yl)methylene)hydrazine (potassium bromide tabletting KBr, $cm^{-1}$): 2927.0w, 2835.3w, 1660.8s, 1616.1vs, 1586.0s, 1506.1m, 1469.1w, 1455.8w, 1384.5vs, 1352.1w, 1326.6w, 1280.6w, 1264.7m, 1214.4m, 1114.8s, 1041.3m, 1019.3m, 971.1m, 841.1m, 841.1m, 659.4m, 627.3w, 496.4m; copper-1,2-bis((5H-imidazol-4-yl)methylene)hydrazine (potassium bromide tabletting KBr, $cm^{-1}$): 2917.4w, 2853.4w, 1654.8s, 1610.5vs, 1577.3s, 1500.0w, 1458.1w, 1384.3vs, 1252.2m, 1201.7w, 1114.4s, 1050.4m, 1017.9m, 968.2w, 840.8m, 818.0m, 653.3m, 619.3w, 561.5w, 504.8w; manganese-1,2-bis((5H-imidazol-4-yl)methylene)hydrazine (potassium bromide tabletting KBr. $cm^{-1}$): 2920.64w, 1655.6s, 1604.7vs, 1584.1s, 1568.4s, 1515.78m, 1495.4m, 1467.7w, 1415.1w, 1386.8m, 1349.5s, 1276.5w, 1252.2s, 1206.9m, 1111.2s, 1028.2m, 1005.2m, 963.3m, 855.18w, 838.5m, 816.5m, 791.3m, 754.6m, 733.1w, 695.6w, 659.8s, 627.2m, 487.9m; nickel-bis-1,2-bis ((5H-imidazol-4-yl)methylene)hydrazine (potassium bromide tabletting KBr, $cm^{-1}$): 2920.6w, 1654.7s, 1600.3vs, 1570.3s, 1498.1m, 1458.9w, 1437.9w, 1408.9w, 1384.9m, 1355.8m, 1327.6w, 1258.7s, 1198.8m, 1111.2s, 1044.7m, 1014.3s, 964.3m, 840.9m, 818.2m, 660.6m, 640.2w, 499.9m.

Crystals of the zeolite porous metal bis(imidazole) coordination polymers of the present invention belong to a cubic system. Space group is: Ia $\bar{3}$ d, cell parameters are: zinc-1,2-bis((5H-imidazol-4-yl)methylene)hydrazine: a=b=c=34.6471(2) Å, α=β=γ=90°, V=41591.1(4) Å$^3$; copper-1,2-bis((5H-imidazol-4-yl)methylene)hydrazine: a=b=c=34.2896(3) Å, a=b=g=90°, V=40316.8(6) Å$^3$; manganese-1,2-bis((5H-imidazol-4-yl)methylene)hydrazine: a=b=c=35.7950(4) Å, α=β=γ=90°, V=45863.4(9) Å$^3$; nickel-1,2-bis((5H-imidazol-4-yl)methylene)hydrazine: a=b=c=33.8514(19) Å, α=β=γ=90°, V=38791(4) Å$^3$. The four coordination polymers have the same framework structure, and only differ in that the metal atom is different. Among the four types of coordination polymers, apart from the metal atom in the nickel-1,2-bis((5H-imidazol-4-yl)methylene)hydrazine adopting a six-coordinate octahedral configuration (one additional water ligand), the metal atoms of the remaining three coordination polymers adopt a five-coordinate square planar pyramidal configuration. The structure is based on a bridged coordination of the ligand BIm and metal ions forming a three-dimensional framework of three-dimensional channels having left-handed and right-handed spirals mirroring each other. The channels are filled with DMF or ethanol solvent molecules, and the framework structure has the same three-dimensional topological network structure as the BSV zeolite.

The method of synthesizing the zeolite coordination polymers of the present invention comprises the following methods: method 1: Dissolving a mixture of the organic ligand BIm and a metal salt ($Zn(NO_3)_2 \cdot 6H_2O$, $Cu(NO_3)_2 \cdot 3H_2O$, $Ni(NO_3)_2 \cdot 6H_2O$ or $Mn(NO_3)_2$ (50% aqueous solution)) in DMF or a mixed solvent of DMF/ethanol. The reaction is carried out under solvothermal conditions, and then the solution is filtered, the crystals are collected, washed with DMF, and then dried. The molar ratio of the described BIm to the metal salt was from 1:1 to 1.1:1, with a preferred molar ratio of 1:1.

The volume ratio of the DMF and ethanol is from 4:1 to 3:1. with a preferred volume ratio of 4:1.

The heating temperature is from 100 to 120° C.

Method 2: Dissolving an organic ligand and $Zn(NO_3)_2 \cdot 6H_2O$ in DMF, and slowly diffuse at room temperature using a mixed solvent of triethylamine/n-hexane, followed by filtration. The precipitate is collected, washed using DMF and dried.

The volume ratio of the described triethylamine and n-hexane is from 2:70 to 5:70, with a preferred volume ratio of 3:70.

Thermal analysis experiments show clearly that ligand frameworks of the coordination polymers have a high thermal stability (see FIGS. 1, 2, 3 and 4), and gas adsorption experiments show clearly that they have a strong adsorption capacity for carbon dioxide under conditions of 0° C. and atmospheric pressure, achieving an adsorption capacity of 70.2 milliliters per gram, or an adsorption capacity of 138.0 milligrams of carbon dioxide per gram. Hence, such coordination polymers can be used as potential carbon storage material, and has favorable application prospects in the field of materials science.

To enable a further understanding of said objectives and the technological methods of the invention herein, a brief description of the drawings is provided below followed by a detailed description of the preferred embodiments.

DETAILED DESCRIPTION OF THE PREFERRED EMBODIMENTS

Figure 1:
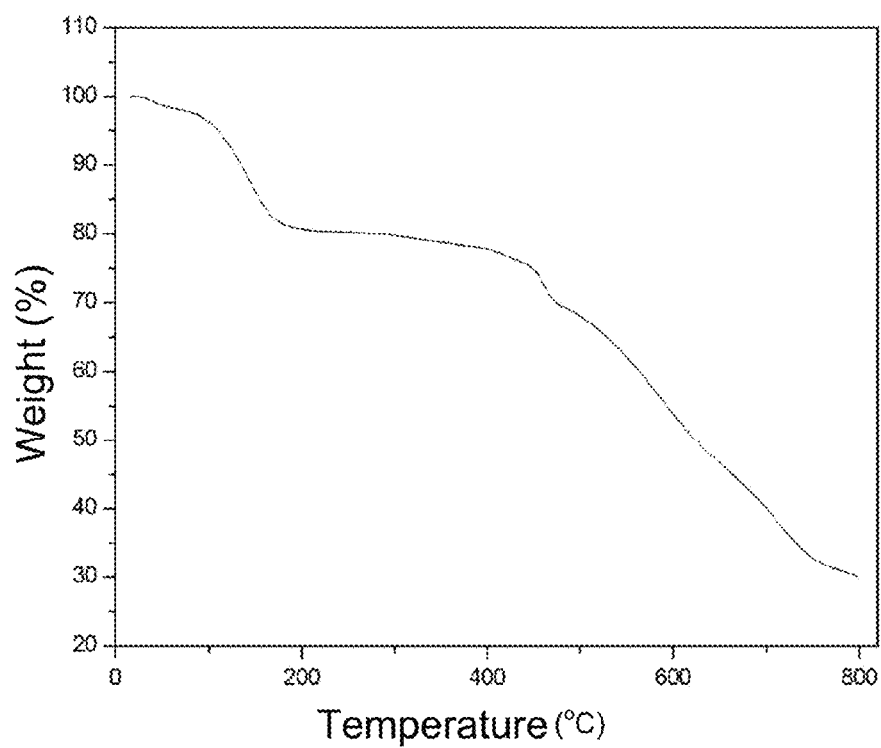
FIG. 1 shows a thermogram of zinc-1,2-bis((5H-imidazol-4-yl)methylene)hydrazine of the present invention.
Figure 2:
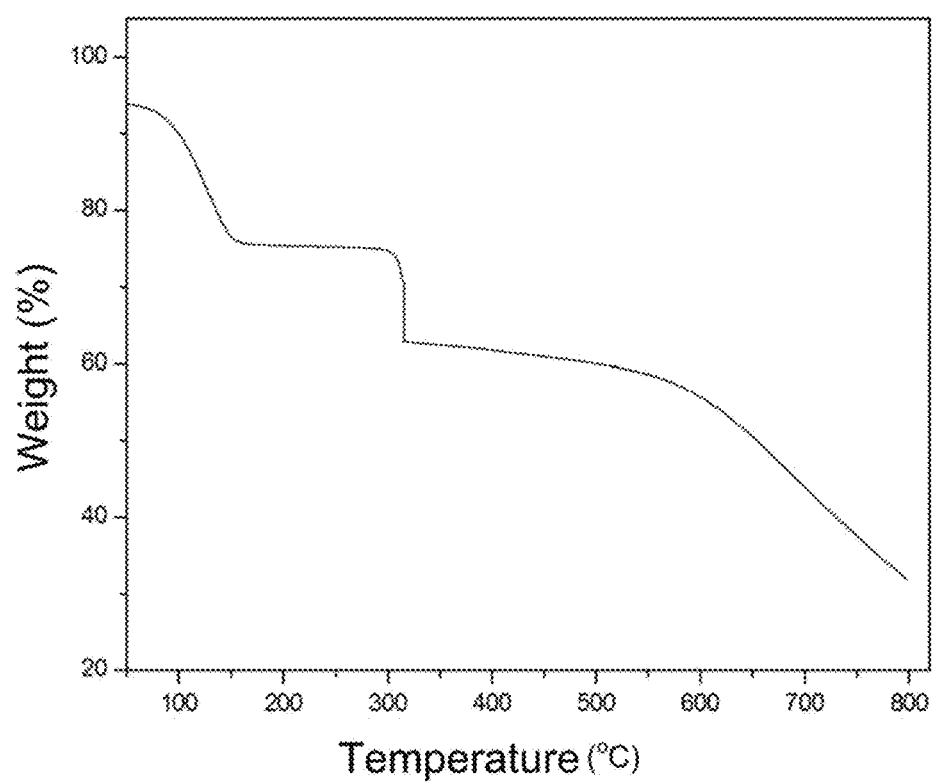
FIG. 2 shows a thermogram of copper-1,2-bis((5H-imidazol-4-yl)methylene)hydrazine of the present invention.
Figure 3:
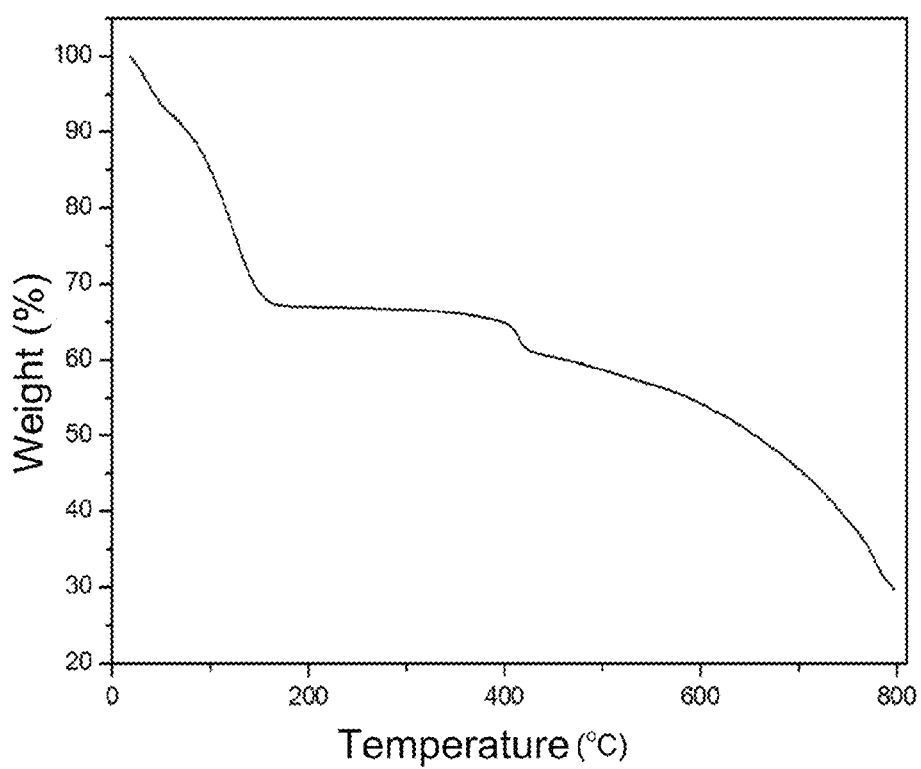
FIG. 3 shows a thermogram of manganese-1,2-bis((5H-imidazol-4-yl)methylene)hydrazine of the present invention.
Figure 4:
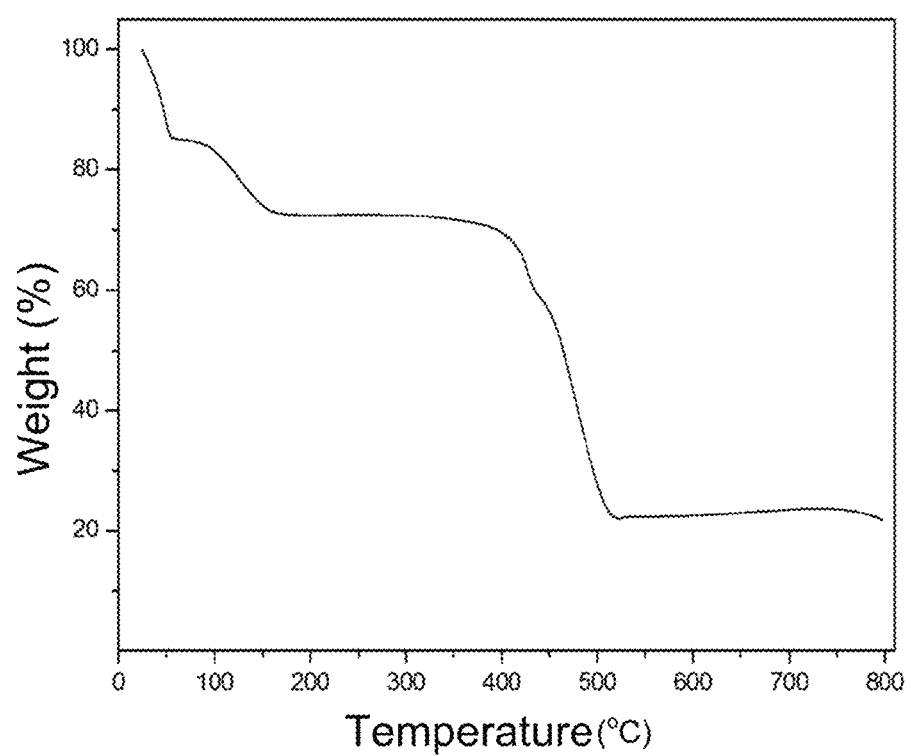
FIG. 4 shows a thermogram of nickel-1,2-bis((5H-imidazol-4-yl)methylene)hydrazine of the present invention.

Thermal analysis experiments show clearly that ligand frameworks of the coordination polymers have a high thermal stability (see FIGS. 1, 2, 3 and 4), and gas adsorption experiments show clearly that they have a strong adsorption capacity for carbon dioxide under conditions of 0° C. and atmospheric pressure, achieving an adsorption capacity of 70.2 milliliters per gram, or an adsorption capacity of 138.0 milligrams of carbon dioxide per gram. Hence, such coordination polymers can be used as potential carbon storage material, and has favorable application prospects In the field of materials science.

Embodiments of the Coordination Polymers

Embodiment 1: 0.021 mmol of BIm (1,2-bis((5H-imidazol-4-yl)methylene)hydrazine) and 0.021 mmol of $Zn(NO_3)_2 \cdot 6H_2O$ were dissolved in 2.0 mL of DMF (N,N-dimethyl formamide) solvent, poured into a hard glass tube sealed at one end, and then heated to fuse and seal the glass tube. The sealed glass tube was placed into an oven and heated at a constant temperature of 100 degrees Celsius for 24 hours, after which the crystals were collected, washed with DMF, and then dried to obtain the target product. The yield was 50%.

Embodiment 2: 1.94 mmol of BIm and 1.94 mmol of $Zn(NO_3)_2 \cdot 6H_2O$ were dissolved in 90 mL of DMF solvent, this mixture was then used to separately fill 10 small glass bottles. Each glass bottle contained 9.0 mL of the mixture, and were placed into a wide-mouth bottle (500 mL) filled with a mixed solvent of triethylamine/n-hexane (73 mL, with a volume ratio of 3/70), and slow diffusion was carried out for three days to obtain the product, which was then washed with DMF and dried to obtain the target product. The yield was 90%.

Embodiment 3: 0.021 mmol of BIm and 0.021 mmol of $Cu(NO_3)_2 \cdot 3H_2O$ were dissolved in 2.0 mL mixed solvent of DMF/ethanol solvent (volume ratio of 4:1), poured into a hard glass tube sealed at one end, and then heated to fuse and seal the glass tube. The sealed glass tube was placed into an oven and heated at a constant temperature of 100 degrees Celsius for 24 hours, after which the crystals collected, washed with DMF, and then dried to obtain the target product. The yield was 60%.

Embodiment 4: 0.021 mmol of BIm and 0.021 mmol of $Mn(NO_3)_2 \cdot 6H_2O$ were dissolved in 2.0 mL mixed solvent of DMF/ethanol (volume ratio of 4:1), poured into a hard glass tube sealed at one end, and then heated to fuse and seal the glass tube. The sealed glass tube was placed into an oven and heated at a constant temperature of 120 degrees Celsius for 24 hours, after which the crystals collected, washed with DMF, and then dried to obtain the target product. The yield was 50%.

Embodiment 5: 0.021 mmol of BIm and 0.021 mmol of $Ni(NO_3)_2 \cdot 6H_2O$ were dissolved in 2.0 mL mixed solvent of DMF/ethanol (volume ratio of 4:1), poured into a hard glass tube sealed at one end, and then heated to fuse and seal the glass tube. The sealed glass tube was placed into an oven and heated at a constant temperature of 120 degrees Celsius for 24 hours, after which the crystals collected, washed with DMF, and then dried to obtain the target product. The yield was 55%.

Figure 5:
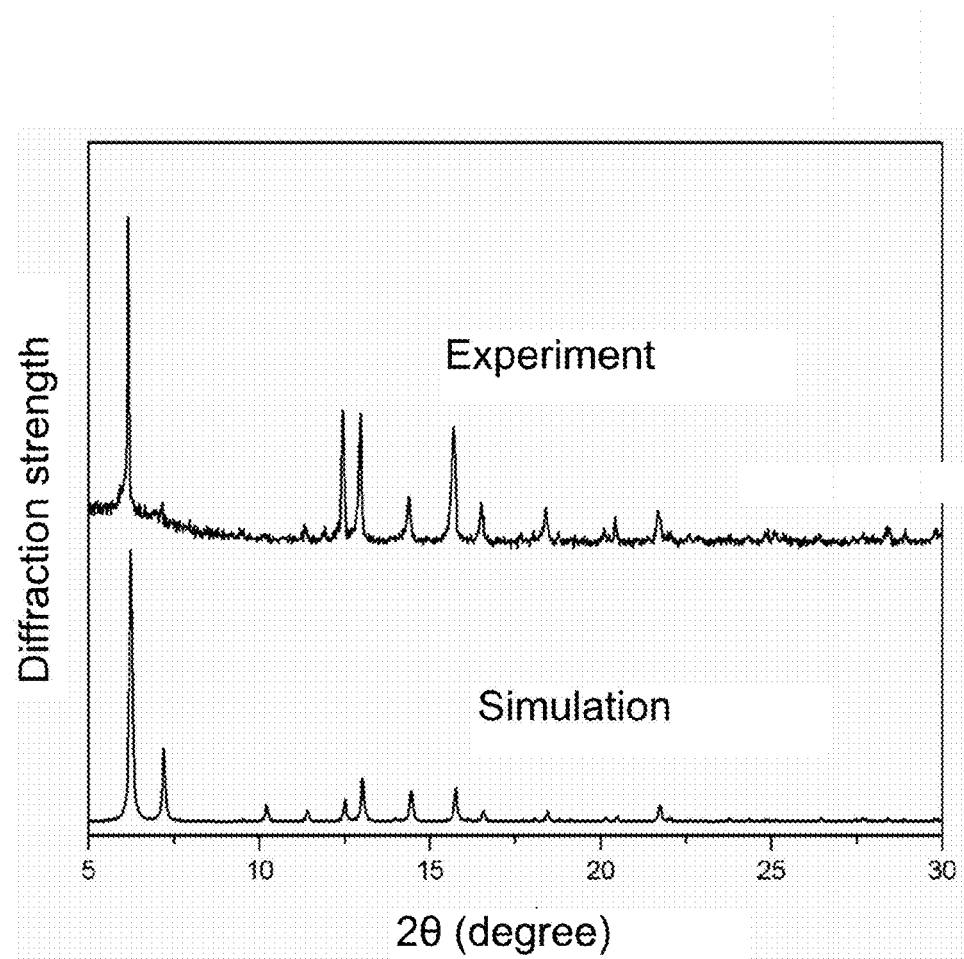
FIG. 5 shows a powder diffraction pattern of zinc-1,2-bis ((5H-imidazol-4-yl)methylene)hydrazine of the present invention.
Figure 6:
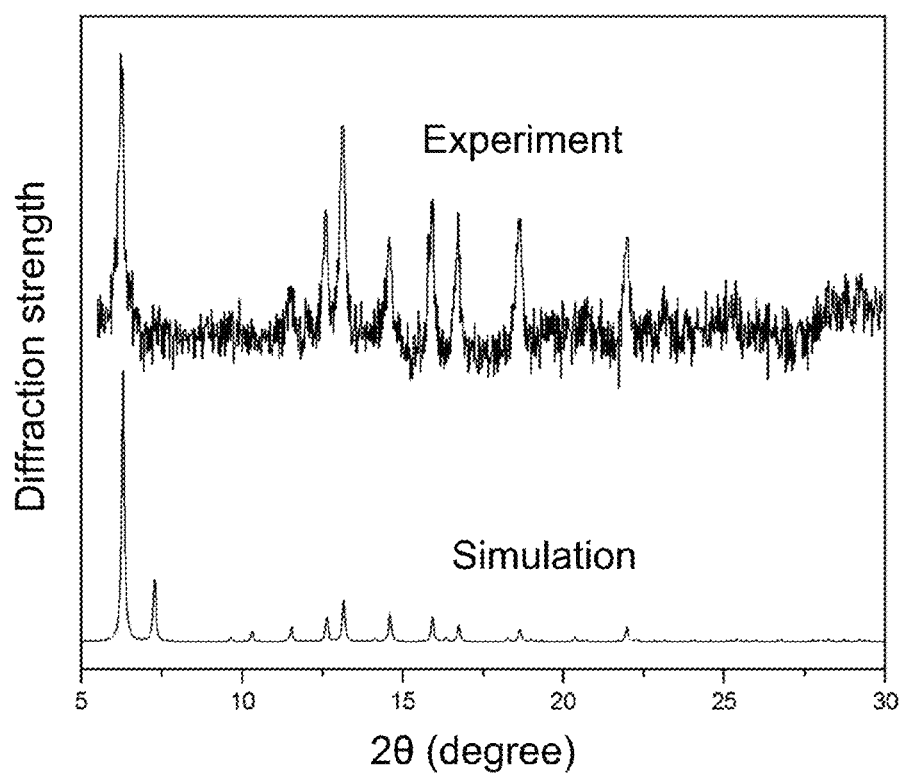
FIG. 6 shows a powder diffraction pattern of copper-1,2-bis((5H-imidazol-4-yl)methylene)hydrazine of the present invention.
Figure 7:
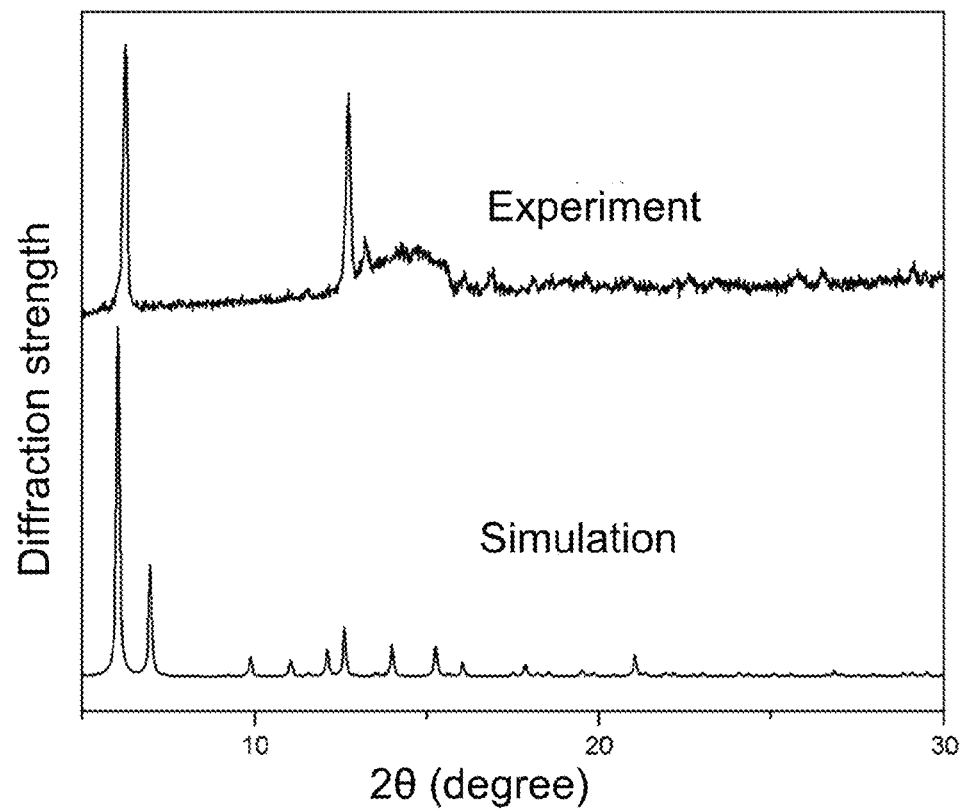
FIG. 7 shows a powder diffraction pattern of manganese-1,2-bis((5H-imidazol-4-yl)methylene)hydrazine of the present invention.
Figure 8:
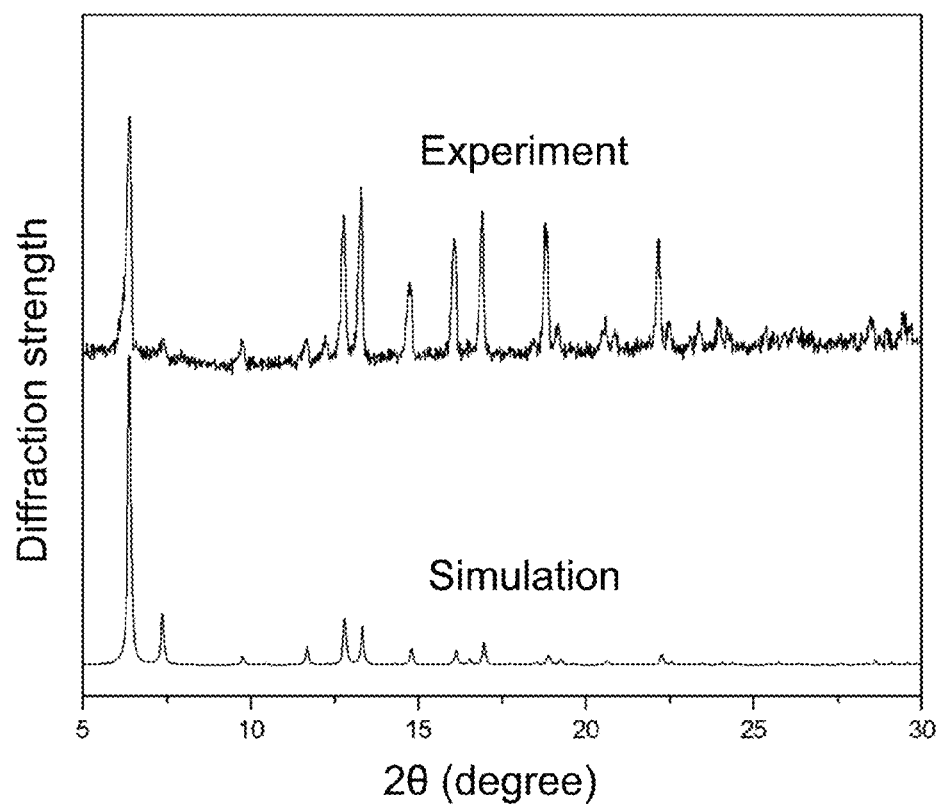
FIG. 8 shows a powder diffraction pattern of nickel-1,2-bis((5H-imidazol-4-yl)methylene)hydrazine of the present invention.

Embodiment 6: The characteristics and adsorption properties of zeolite porous metal Bis(imidazole) coordination polymers: (1) Powder diffraction characteristics and purity. FIG. 5 shows these properties for zinc-1,2-bis((5H-imidazol-4-yl)methylene)hydrazine. FIG. 6 shows these properties for copper-1,2-bis((5H-imidazol-4-yl)methylene)hydrazine. FIG. 7 is a powder diffraction pattern of manganese-1,2-bis((5H-imidazol-4-yl)methylene)hydrazine. FIG. 8 is a powder diffraction pattern of nickel-1,2-bis((5H-imidazol-4-yl)methylene)hydrazine. Powder diffraction data was collected on a Bruker D8 Advance diffractometer. The operating voltage of the instrument was 40 KV (kilovolt), current was 40 mA, and used graphite monochromatic copper target X-rays (Cu Kα, λ=1.5418 Å). Continuous scanning was completed within a range of 5° to 30°, and Mercury software was used for digital-to-analog conversion of the crystal structure powder diffraction spectra.

Figure 9:
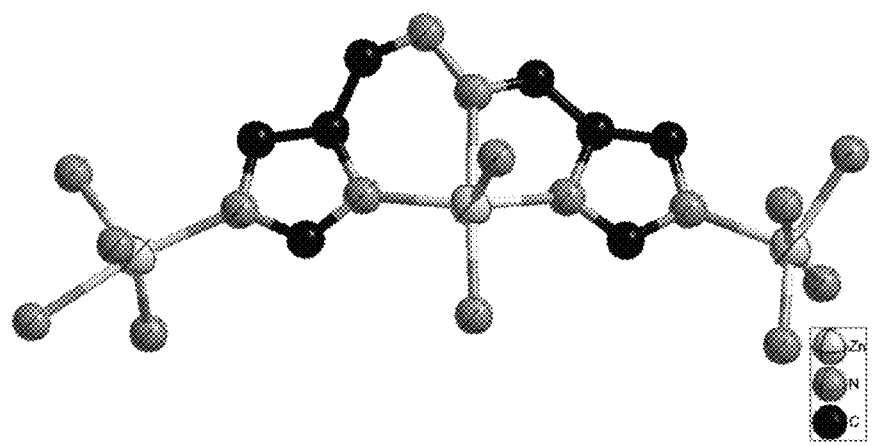
FIG. 9 shows a coordination environment of zinc-1,2-bis ((5H-imidazol-4-yl)methylene)hydrazine of the present invention.
Figure 10:
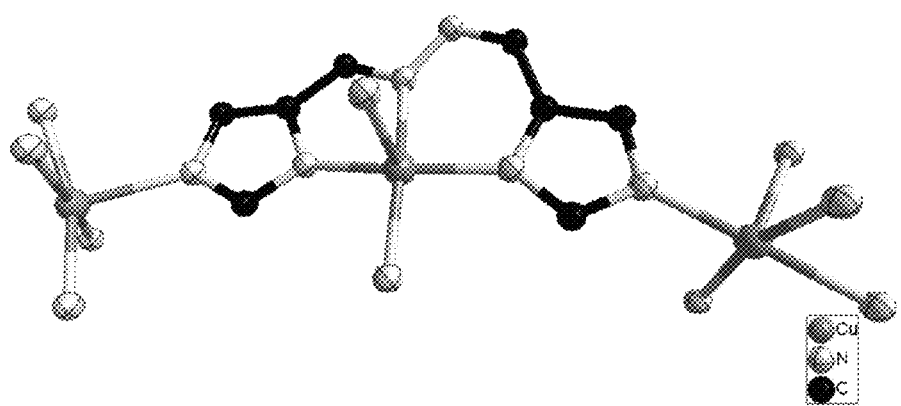
FIG. 10 shows a coordination environment of copper-1,2-bis((5H-imidazol-4-yl)methylene)hydrazine of the present invention.
Figure 11:
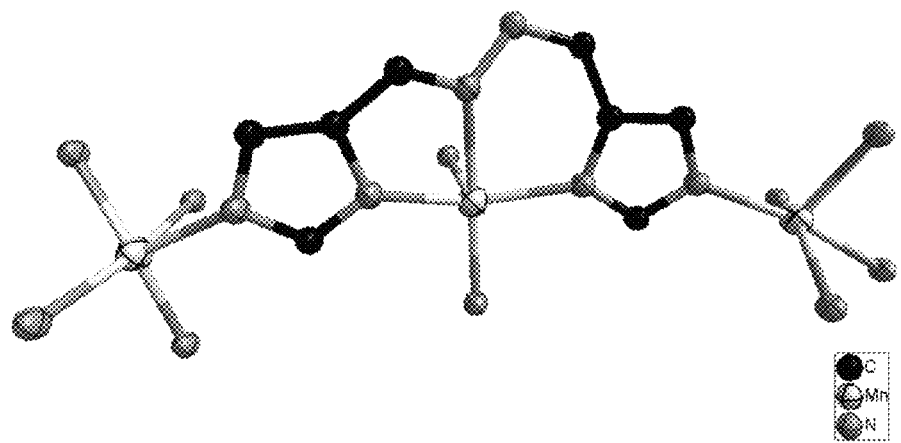
FIG. 11 shows a coordination environment of manganese-1,2-bis((5H-imidazol-4-yl)methylene)hydrazine of the present invention.
Figure 12:
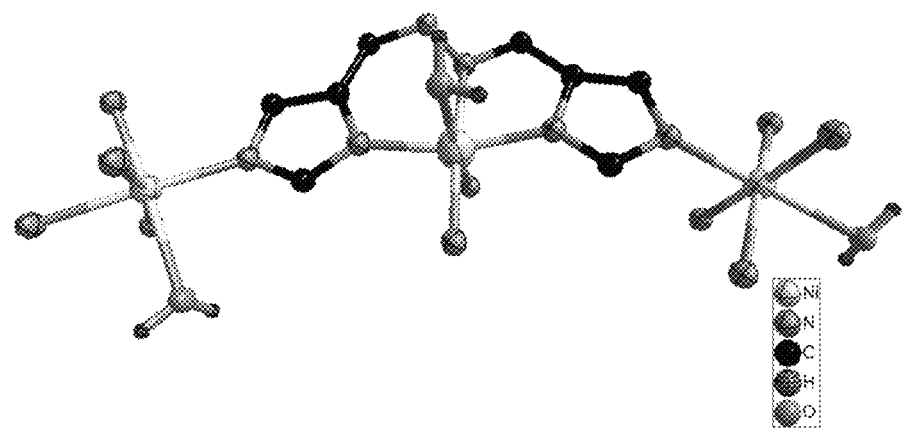
FIG. 12 shows a coordination environment of nickel-1,2-bis((5H-imidazol-4-yl)methylene)hydrazine of the present invention.
Figure 13:
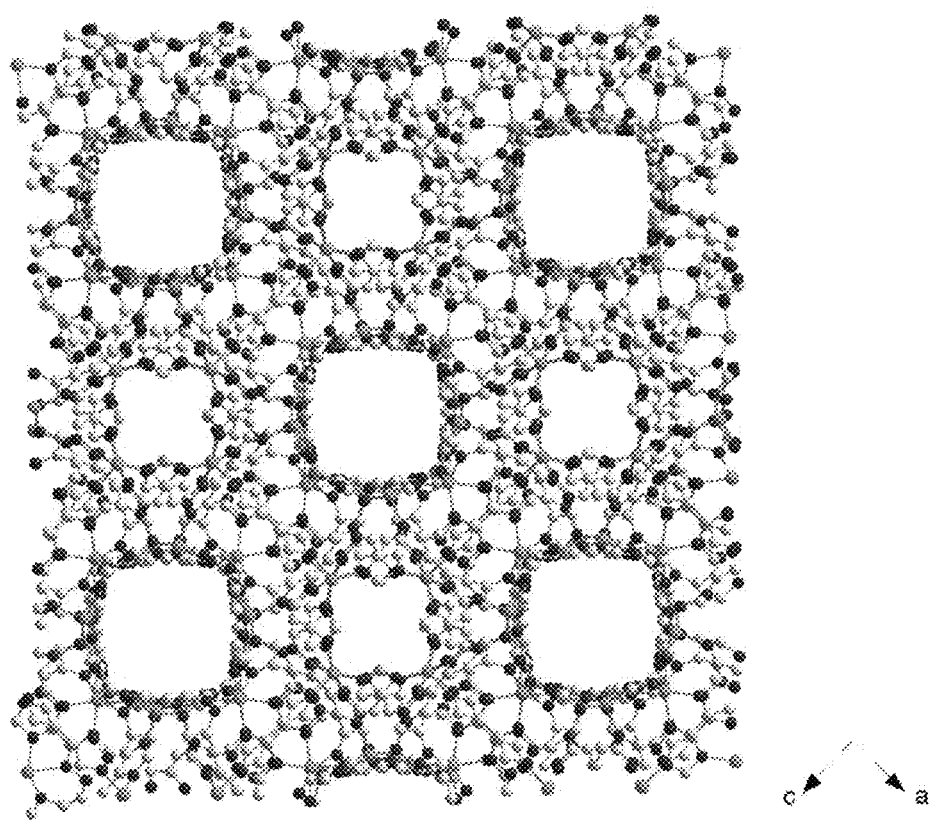
FIG. 13 shows a three-dimensional porous structure of a zeolite metal (zinc, copper, manganese, nickel) bis(imidazole) coordination polymer.

(2) Determination of Crystal Structure: The appropriate crystal size was selected under a microscope. The X-rays were monochromatized by passing through a graphite monochromator on an Agilent's Gemini A diffractometer (Cu Kα, λ=1.5418 Å), and the data was processed using the diffractometer program CrysAlis$^{Pro.1}$. A direct method was used to determine the initial structure model. Then the structure was refined using a method of least squares based on F2. Each isometric refinement was carried out on all non-hydrogen atoms, and theoretical hydrogenation was used to confirm the position of the hydrogen atoms. Guest molecules lay in a highly disordered state, and was processed using the SQEEZE program of the PLATON software. As for the crystal structural drawings: FIG. 9 shows zinc-1,2-bis((5H-imidazol-4-yl)methylene)hydrazine; FIG. 10 shows copper-1,2-bis((5H-imidazol-4-yl)methylene)hydrazine; FIG. 11 shows manganese-1,2-bis((5H-imidazol-4-yl)methylene)hydrazine; FIG. 12 shows the coordination environment of nickel-1,2-bis((5H-imidazol-4-yl)methylene)hydrazine; FIG. 13 shows the three-dimensional porous structure of the zeolite metal (zinc, copper, manganese or nickel) bis(imidazole) coordination polymer. A portion of parameters of collected crystallographic diffraction data and structure refinements are listed in Table 1.

Figure 14:
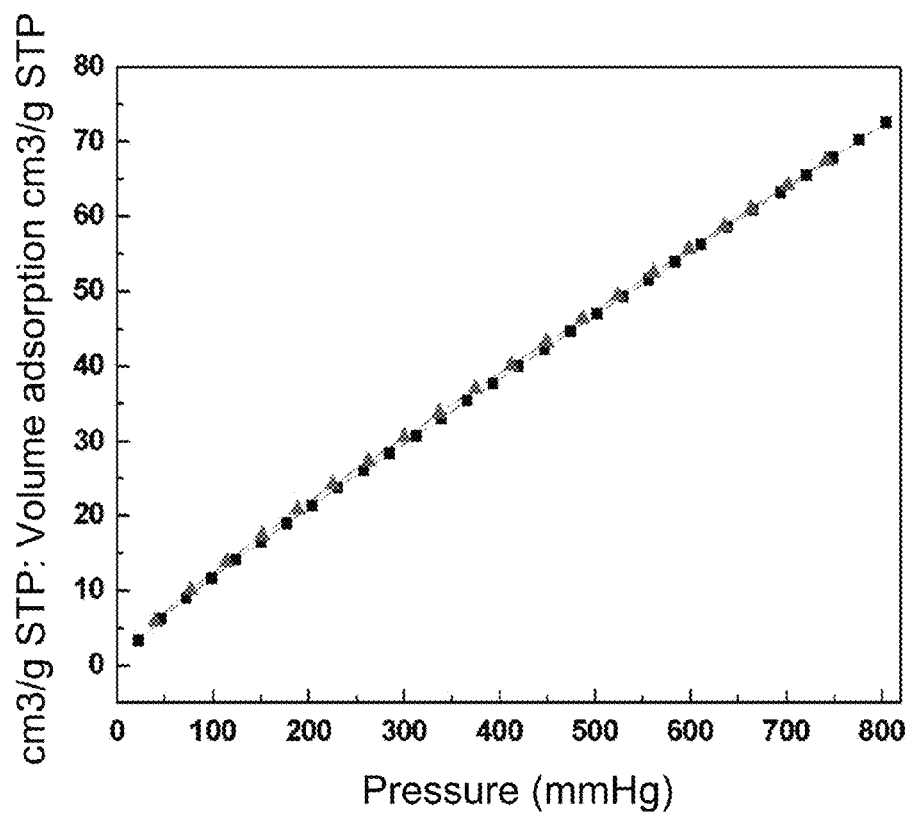
FIG. 14 shows a carbon dioxide adsorption/desorption plot of zinc-1,2-bis((5H-imidazol-4-yl)methylene)hydrazine of the present invention.
Figure 15:
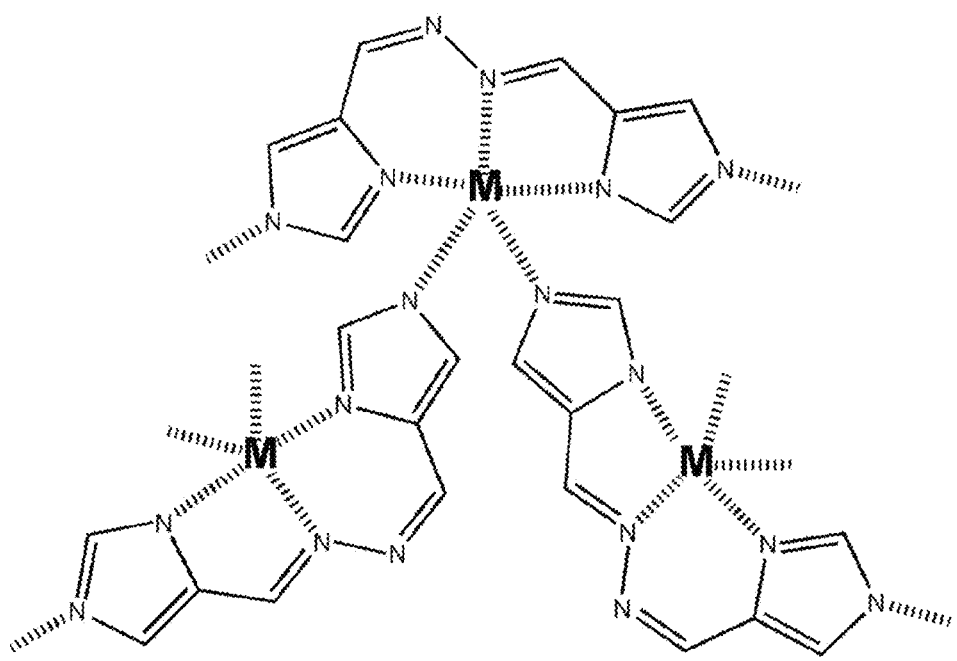
FIG. 15 is a structural schematic view of a polymer of the present invention.
Figure 16:
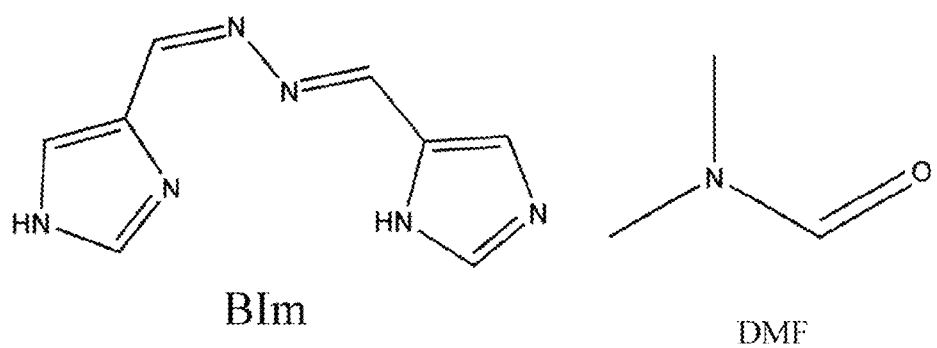
FIG. 16 shows structural schematic views of BIm (1,2-bis ((5H-imidazol-4-yl)methylene)hydrazine) and DMF (N,N-dimethyl formamide) of the present invention.

(3) Regarding adsorption performance studies of the coordination polymers of embodiment 1: Carbon dioxide adsorption experiments were completed using the U.S. Micromeritics ASAP 2010 volumetric adsorption apparatus. Adsorption and desorption experiments were completed on 190.1 mg of zinc-1,2-bis((5H-imidazol-4-yl)methylene)hydrazine samples below 0 degrees using high purity carbon dioxide gas. The results are shown in FIG. 14 (squares represent isothermal adsorption points. Triangles represent isothermal desorption points). FIG. 14 shows complete reversible adsorption and desorption of carbon dioxide by zeolite metal bis(imidazole) coordination polymers of the present invention. Under conditions of normal pressure and zero pressure, 70.2 milliliters of $CO_2$ per gram can be absorbed, which is equivalent to 1 kg of coordination polymers being able to absorb 138.7 grams of $CO_2$. Absorption proportion by weight achieves 13.8%, which surpasses the carbon dioxide adsorption capacity of general zeolite metal imidazole polymers, such as ZIF-69, which has the strongest carbon dioxide adsorption capacity, being able to adsorb 126.1 g per kg under conditions of normal pressure and 0° C. (Banerjee, R.; Phan, A.; Wang, B.; Knobler, C.; Furukawa, H.; O'Keeffe, M.; Yaghi, O M Science 2008, 319, 939-943).

TABLE 1

Crystallographic data for zeolite porous metal imidazole coordination polymers.

|  | zinc-1,2-bis((5H-imidazol-4-yl)methylene)hydrazine | copper-1,2-bis((5H-imidazol-4-yl)methylene)hydrazine | manganese-1,2-bis((5H-imidazol-4-yl)methylene)hydrazine | nickel-1,2-bis((5H-imidazol-4-yl)methylene)hydrazine |
|---|---|---|---|---|
| Empirical Formula | $C_{384}H_{288}N_{288}Zn_{48}$ | $C_{384}H_{288}N_{288}Cu_{48}$ | $C_{384}H_{288}N_{288}Mn_{48}$ | $C_{384}H_{384}N_{288}Ni_{48}O_{48}$ |
| Molecular weight | 12074.78 | 11986.94 | 11574.14 | 12619.87 |
| Crystal system | cubic | cubic | cubic | cubic |
| Temperature (K) | 293.3 | 293.3 | 293.3 | 100.0 |
| Space group | Ia3 d | Ia3 d | Ia3 d | Ia3 d |
| Cell parameters |  |  |  |  |
| a (Å) | 34.6471(2) | 34.2896(3) | 35.7950(4) | 33.8514(19) |
| b (Å) | 34.6471(2) | 4.2896(3) | 35.7950(4) | 33.8514(19) |
| c (Å) | 34.6471(2) | 34.2896(3) | 35.7950(4) | 33.8514(19) |
| α (deg) | 90 | 90 | 90 | 90 |
| β (deg) | 90 | 90 | 90 | 90 |
| γ (deg) | 90 | 90 | 90 | 90 |
| V (Å$^3$) | 41591.1(4) | 40316.8(6) | 45863.4(9) | 38791(4) |
| Z | 2 | 2 | 2 | 2 |
| Theoretical density (g cm$^{-3}$) | 0.964 | 0.987 | 0.838 | 1.080 |

TABLE 1-continued

Crystallographic data for zeolite porous metal imidazole coordination polymers.

| | zinc-1,2-bis((5H-imidazol-4-yl)methylene)hydrazine | copper-1,2-bis((5H-imidazol-4-yl)methylene)hydrazine | manganese-1,2-bis((5H-imidazol-4-yl)methylene)hydrazine | nickel-1,2-bis((5H-imidazol-4-yl)methylene)hydrazine |
|---|---|---|---|---|
| Absorption coefficient ($mm^{-1}$) | 1.858 | 1.722 | 5.518 | 1.689 |
| Total diffraction points | 10396 | 15159 | 15968 | 14980 |
| Independent diffraction points | 2132 | 3325 | 3099 | 2627 |
| $R_{int}$ | 0.0650 | 0.0278 | 0.0788 | 0.1054 |
| $R_1 [I > 2\sigma(I)]^a$ | 0.0388 | 0.0407 | 0.0513 | 0.1289 |
| $wR_2 [I > 2\sigma(I)]^b$ | 0.0791 | 0.1148 | 0.1117 | 0.3104 |
| $R_1$ [all data] | 0.0766 | 0.0510 | 0.1183 | 0.1852 |
| $wR_2$ [all data] | 0.0888 | 0.1214 | 0.1302 | 0.3708 |

$^a R_1 = å(||F_0| - |F_c||)/å|F_0|$; $^b wR_2 = [åw(F_0^2 - F_c^2)^2/åw(F_0^2)^2]^{1/2}$

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. A zeolite porous metal bis(imidazole) coordination polymer having the following general chemical formula:

$\{[M(BIm)]\cdot xDMF\cdot yC_2H_6O\cdot zH_2O\}_\infty$, wherein:

M is selected from the group consisting of Zn, Cu, Mn and Ni, and when M=Zn, x=0.9, y=0, z=0;

when M=Cu, x=1.2, y=0, z=0;

when M=Mn, x=2.0, y=0, z=0; and when M=Ni, x=0.4, y=1.2, z=1.0, and wherein BIm is 1,2-bis((5H-imidazol-4-yl)methylene)hydrazine, and DMF is N,N-dimethyl formamide.

2. The porous coordination polymers according to claim 1, wherein crystals of the zeolite porous metal bis(imidazole) coordination polymers belong to a cubic system, the space group is Ia$\bar{3}$d, and the cell parameters are:

zinc 1,2-bis((5H-imidazol-4-yl)methylene)hydrazine: a=b=c=34.6471(2) Å, α=β=γ=90°, V=41591.1(4) Å$^3$;

copper-1,2-bis((5H-imidazol-4-yl)methylene)hydrazine: a=b=c=34.2896(3) Å, α=β=γ=90°, V=40316.8(6) Å$^3$;

manganese-1,2-bis((5H-imidazol-4-yl)methylene)hydrazine: a=b=c=35.7950(4) Å, α=β=γ=90°, V=45863.4(9) Å$^3$;

nickel-1,2-bis((5H-imidazol-4-yl)methylene)hydrazine: a=b=c=33.8514(19), α=β=γ=90°, V=38791(4) Å$^3$; wherein metal atoms of the nickel-1,2-bis((5H-imidazol-4-yl)methylene)hydrazine adopt a six-coordinate octahedral configuration; metal atoms of zinc-bis-4-imidazole methylene hydrazine, copper-bis-4-imidazole methylene hydrazine, and manganese-bis-4-imidazole methylene hydrazine polymers all adopt a five-coordinate square planar pyramidal configuration; the crystals' structure of the porous metal bis(imidazole) coordination polymer is based on a bridged coordination of the ligand BIm and the metal ions forming a three-dimensional framework of three-dimensional channels having left-handed and right-handed spirals mirroring each other; the three-dimensional channels are filled with DMF or ethanol solvent molecules; and the three-dimensional framework structure has the same three-dimensional topological network structure as the BSV zeolite.

3. A preparation method of the coordination polymers of claim 1, wherein the preparation procedure has the following steps: mixing the organic ligand BIm and corresponding metal salts according to a molar ratio of 1:1 to 1.1:1, then dissolving in a mixed solvent of DMF/ethanol, allowing a reaction to occur under solvothermal conditions; filtering the solution, collecting the crystals, washing with DMF, and then drying, and wherein the metal salts are respectively Zn(NO$_3$)$_2$·6H$_2$O, Cu(NO$_3$)$_2$·3H$_2$O, Mn(NO$_3$)$_2$ or Ni(NO$_3$)$_2$·6H$_2$O.

4. The preparation method of the coordination polymers of claim 3, wherein the ratio by volume of the DMF and ethanol is from 4:1 to 3:1.

5. The preparation method of the coordination polymers of claim 4, wherein a heating-up temperature condition of the solvent is from 100 to 120° C.

6. A preparation method of the coordination polymers of claim 1, wherein the preparation procedures of the zinc-1,2-bis((5H-imidazol-4-yl)methylene)hydrazine have the following steps: dissolving the organic ligand BIm and Zn(NO$_3$)$_2$·6H$_2$O in DMF according to a molar ratio of from 1:1 to 1.1:1, slowly diffusing using a mixed solvent of triethylamine/n-hexane at room temperature, followed by filtrating, collecting precipitate, washing with DMF, and then drying.

7. The preparation method of the coordination polymers of claim 6, wherein the volume ratio of the triethylamine and n-hexane is from 3:70 to 5:70.

* * * * *